United States Patent [19]
Nilsson et al.

[11] Patent Number: 4,934,358
[45] Date of Patent: Jun. 19, 1990

[54] DEVICE FOR SELF-ADMINISTRATION OF PHYSIOLOGICALLY ACTIVE SUBSTANCES, WITH PREVENTION OF OVERDOSING

[75] Inventors: Sven-Erik Nilsson, Döbeliusvägen 39, S-253 67 Helsingborg; Ove B. Fernö, Helsingborg; Jan E. Lilja, Kristianstad, all of Sweden

[73] Assignee: Sven-Erik Nilsson *

[21] Appl. No.: 250,691

[22] PCT Filed: Mar. 20, 1987

[86] PCT No.: PCT/SE87/00146
§ 371 Date: Nov. 18, 1988
§ 102(e) Date: Nov. 18, 1988

[87] PCT Pub. No.: WO87/05813
PCT Pub. Date: Oct. 8, 1987

[30] Foreign Application Priority Data
Mar. 24, 1986 [SE] Sweden ............................. 8601351

[51] Int. Cl.$^5$ ..................... A61M 11/00; A61M 16/00
[52] U.S. Cl. ........................ 128/200.23; 128/202.22; 128/203.13
[58] Field of Search ................. 128/200.14, 200.23, 128/204.19, 204.21, 203.12, 203.13, 203.14, 203.23, 203.24, 200.11, 200.12, 200.13, 200.21, 200.22, 200.24, 202.21, 203.15, 204.11

[56] References Cited

U.S. PATENT DOCUMENTS

| | | | |
|---|---|---|---|
| 4,106,503 | 8/1978 | Rosenthal et al. | 128/203.12 |
| 4,393,884 | 7/1983 | Jacobs | 128/200.23 |
| 4,462,398 | 7/1984 | Durkan et al. | 128/200.14 |
| 4,817,822 | 4/1989 | Rand et al. | 128/200.23 |

FOREIGN PATENT DOCUMENTS

WO86/02275 4/1986 PCT Int'l Appl. ............ 128/200.23

Primary Examiner—Edgar S. Burr
Assistant Examiner—Kimberly L. Asher
Attorney, Agent, or Firm—Burgess, Ryan and Wayne

[57] ABSTRACT

A device for self-administration of physiologically active substances without the occurrence of overdosing, includes a container accommodating at least one substance and propellant means for propelling the substances out of the container, nozzle means connected to the container for discharging a substance, a valve connected between the nozzle and the container such that a predetermined amount of the substance is propelled from the container each time the valve has been opened, and manually activated electronic control means for opening the valve in response to manual activation of the electronic control means and for preventing opening of the valve greater than a predetermined number of times within a predetermined time period.

4 Claims, 3 Drawing Sheets

DEVICE FOR SELF-ADMINISTRATION OF PHYSIOLOGICALLY ACTIVE SUBSTANCES, WITH PREVENTION OF OVERDOSING

The present invention relates to a device, preferably in the form of a nose or lung spray, for self-administration of physiologically active substances, with prevention of overdosing, comprising a container accommodating at least one substance, and a propellant, preferably a propellant gas, adapted to propel the substance out of the container, a nozzle connected to said container for discharging the substance, and a valve connected between said nozzle and said container.

There exist a number of applications in which the possibility of self-administration of physiologically active substances, such as drugs, in a predetermined quantity per unit of time is desired, thereby to prevent dangerous overdosing. In the administration of soporifics for example, it would thus be advantageous if, after a dose has been taken, one must wait one or two hours before the next dose can be taken. One way of preventing overdosing is to apply the substance in a matrix which slowly releases the substance under some form of mechanical working. One example of this is the well-known nicotine chewing-gum which is the first antismoking product containing nicotine. Nicotine is absorbed in the oral cavity, and the nicotine is absorbed relatively slowly according as it is released by the chewing-gum. A cigarette smoker absorbs the nicotine much quicker. Already after a couple of minutes, the nicotine/blood concentration has reached a value which is higher than after 20–30 min of chewing a 4 mg nicotine chewing-gum. In spite of this difference in the nicotine absorption, those who wish to give up smoking usually can do so with the assistance of such chewing-gum. However, not all smokers are able to use nicotine chewing-gum, which may be due to chewing difficulties of a mechanical or social nature. Secondary effects may also occur, above all in the gastrointestinal tract.

With the objective of achieving a quicker absorption of nicotine, preventing gastrointestinal secondary effects and facilitating nicotine therapy in antidotal smoking treatment of persons with chewing difficulties, it was attempted to apply in the nose a nicotine-containing viscous solution. These attempts resulted in a quicker nicotine absorption, and nicotine absorption through the nose therefore seems to be an alternative possibility in antidotal smoking treatment. In this connection, it will of course be obvious that the nicotine is administered instead by a nose spray. Using a nose spray would give a more uniform distribution of nicotine over a much larger area, which would result in a quicker and also safer nicotine absorption. A further advantage is that a nose spray is far more easily applicable than a viscous nicotine solution. However, this advantage constitutes an important obstacle to using a nose spray containing nicotine in antidotal smoking treatment since it is far too easy to take repeated doses at more frequent intervals, and combined with the interval between nicotine administration and nicotine absorption, this may easily lead to fits of sickness and dizziness, which could be disastrous for example at the wheel of a motorcar. Also for this reason, nose spray has been deemed unsuitable in the context.

The present invention aims at providing a nose and lung spray with prevention of overdosing.

In its simplest form, an aerosol pack for nose or lung spray comprises a gas container (hereinafter referred to as a dose propellant gas container or merely as a container) having an openable valve. The gas container holds a propellant gas and the chemical substances to be administered. The propellant gas should be a harmless inert gas or, for example, compressed air. The chemical substances in the gas container may be solid or liquid and in the form of a solution, emulsion or suspension. In the gas container an excess pressure prevails. When the valve of the gas container is opened, the propellant gas is expanded by the excess pressure and carries along the physiologically active substances through a narrow outlet in which an aerosol is formed. The propellant gas of the aerosol carries the liquid or solid particles to the absorption surfaces where they adhere. These physiologically active substances are then absorbed through the cellular membranes of the absorption surfaces to act upon the human organism. The outlet, or the extension tube, of the aerosol pack is directed against the surface or the cavity within which the substance is to be absorbed.

The object of the invention is achieved, in the device mentioned by way of introduction, by means of an electronic control member connected to the valve and adapted, upon manual activation, to open said valve during a predetermined period and to prevent, after a predetermined number of doses within a given predetermined space of time, renewed opening of the valve during a similarly predetermined period.

In the present invention, the opening valve on the gas container of the aerosol pack is electrically controlled via a programmable electronic chip having many transistor functions. In a simple embodiment according to the invention, the aerosol pack is supplemented with a battery and a make-and-break electronic contact.

To provide for exact dosing, conventional spray administration utilises a known technique according to which the dose propellant gas container upon manual release is not in direct contact with the nozzle opening, such that only a predetermined dose separated by mechanical means is administered. This spray type may be provided, between the mechanically separated dose and the nozzle opening, with an electronically controlled valve according to the present invention, in which case the manually released and electronically controlled opening time must be sufficiently long to permit emptying of the mechanically predetermined dose.

In a different type of spray pack, the dose-propellant gas container, upon manual release, is in direct contact with the electronically controlled opening valve. In this case, the dose is determined by the valve opening time. Exact dosing is possible on condition that the gas quantity in the gas container is so large that a limited number of propellant gas releases does not affect the released quantity of substance per unit of time. The time during which the valve is open and supplies the user with active substances in an exactly predetermined dose depends upon the type of the active substance, the pressure conditions within the gas container, and pure mechanical constructional problems concerning the valve function. Specific time parameters should be determined for each application of the invention and programmed into the control electronics.

The latitude of electronic programming makes it possible to vary the control schedule of the opening valve in many different ways. If the control electronics are a simple microprocessor, any control schedule may be used which can be translated into an algorithm.

The invention is especially advantageous in that it enables self-administration of highly active substances because the control schedule places an upper limit on the number of doses per unit of time, but also because the electronic construction makes the control schedule entirely inaccessible to the user.

The commonest spray pack of today comprises a container which is provided at one end with an outlet pipe that can be pressed into the said end. When the pipe is pressed into the container, it releases a predetermined dose of the container contents. In accordance with what has been said above, such a spray pack can be provided with a valve controlled in the above-mentioned manner, but the invention is also applicable without the additional valve, by utilising the relative movement between the container and the outlet pipe. Thus, it is possible to use an electronic control member connected with the container and adapted to activate, after a predetermined number of movements of the valve operating member and a corresponding number of doses supplied, a mechanical lock into locking engagement with, alternatively, the valve operating member or the container to prevent relative movement therebetween during a predetermined period.

The invention will now be described in more detail below, reference being had to the accompanying drawings which illustrate schematically an embodiment.

Figure 1:
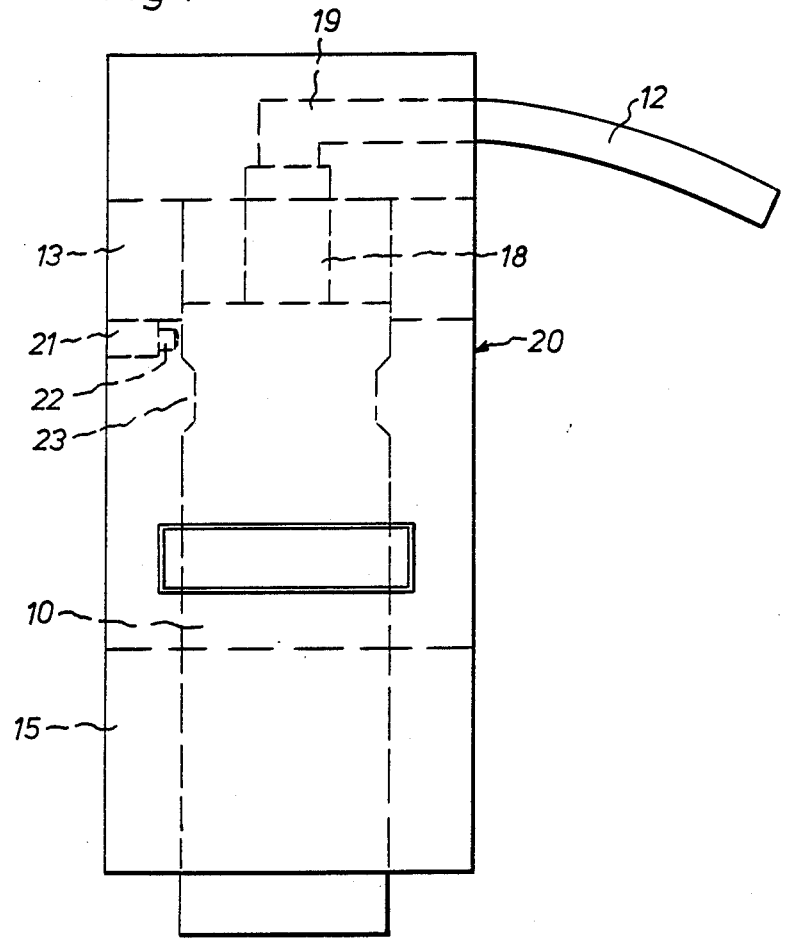
FIG. 1 shows an aerosol device comprising a can of a conventional design.

FIG. 1 shows a gas can of a commercially available type. It comprises a closed cylindrical vessel provided at one end with an outlet pipe 18 which can be depressed a predetermined distance into the end of the vessel to supply a predetermined dose of the substance in the container 10 under the action of a propellant gas. The outlet pipe 18 thus also functions as a valve operating member. The container 10 is accommodated in a downwardly open casing 20 which is so dimensioned that the container end facing away from the outlet pipe projects therefrom. Around the space of the casing 20 adapted to accommodate the container 10, there is arranged an upper annular member accommodating an electronic control member 13 which will be described in more detail below, as well as a lower annular member accommodating a battery 15. The container 10 is displaceable with a suitable running fit in the spaces defined by these members. In its upper end, the casing 20 has a bore accommodating the end of the outlet pipe 18 of the can 10 with a close fit, such that the container is retained in the casing 20 but simultaneously displaceable therein by the relative movement between the container and the pipe 18. The bore accommodating the pipe 18 communicates with a nozzle 12. Thus, the container 10 can be pushed into the casing from the position shown in FIG. 1, whereby the stationary outlet pipe is pressed into the container, and a dose is supplied through said outlet pipe to the nozzle 12.

During each relative movement between the container and the outlet pipe 18 for supplying a dose, the electronic control member 13 senses this movement electrically or mechanically, and when a predetermined number of doses, usually one or two, have been supplied, the member 13 activates a magnet or solenoid 21 to push a lock-forming anchor 22 into engagement with an annular recess in the container 10. Activation is maintained for a predetermined period during which no further relative movement between the container 10 and the pipe 18 can occur, i.e. the container 10 is maintained in the pushed-in position, and no dose can be supplied. The power for operating the circuit 13 is supplied by the battery 15 in the lower annular member.

The invention is also applicable to other types of spray packs in which a dose is supplied by manual activation of a valve operating member which is displaced relative to the container, in that the anchor 22 engages with the container or the valve operating member and prevents relative movement therebetween and thus the supply of a dose.

Figure 2:
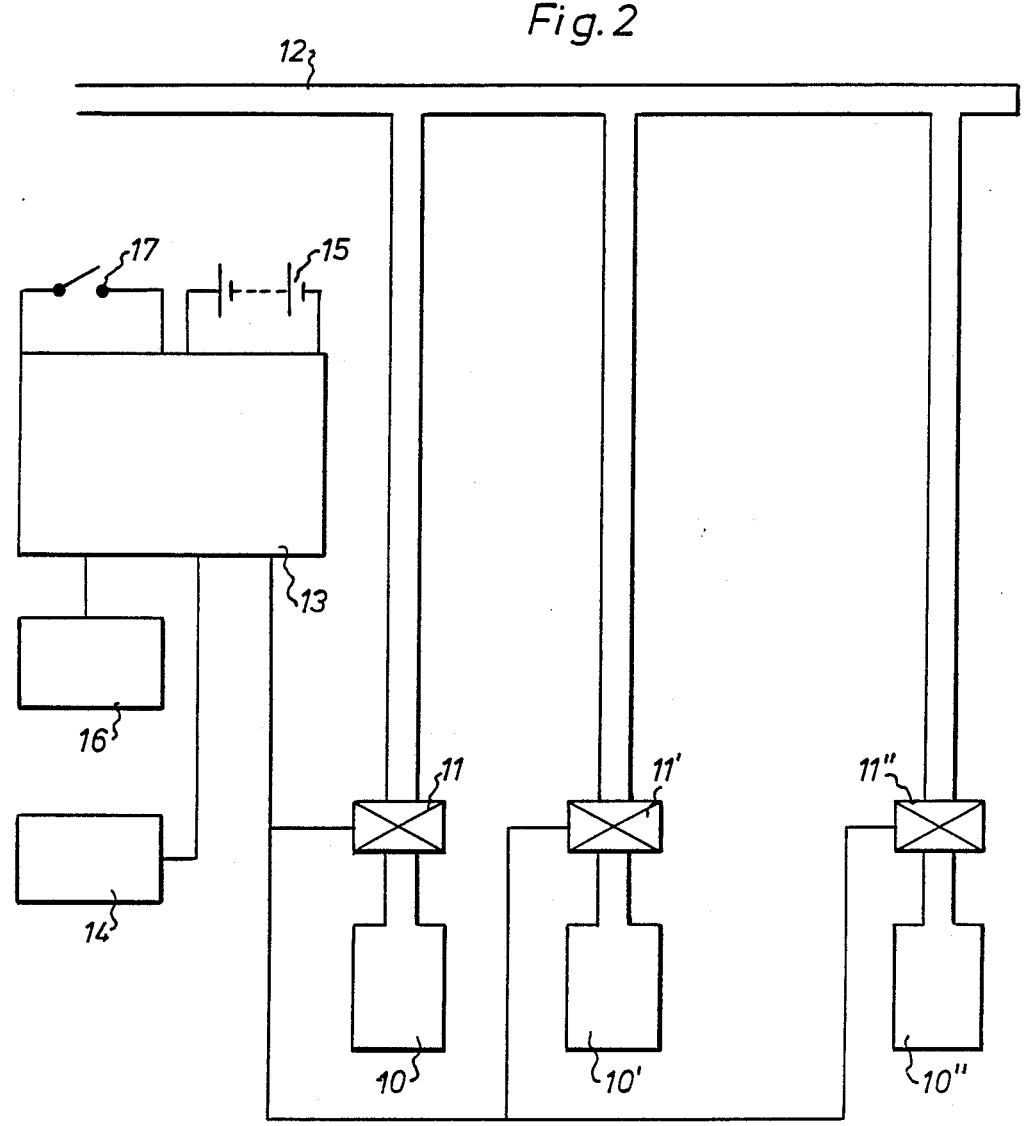
FIG. 2 shows a device having a container of a different design and illustrates the functional construction.
Figure 3:
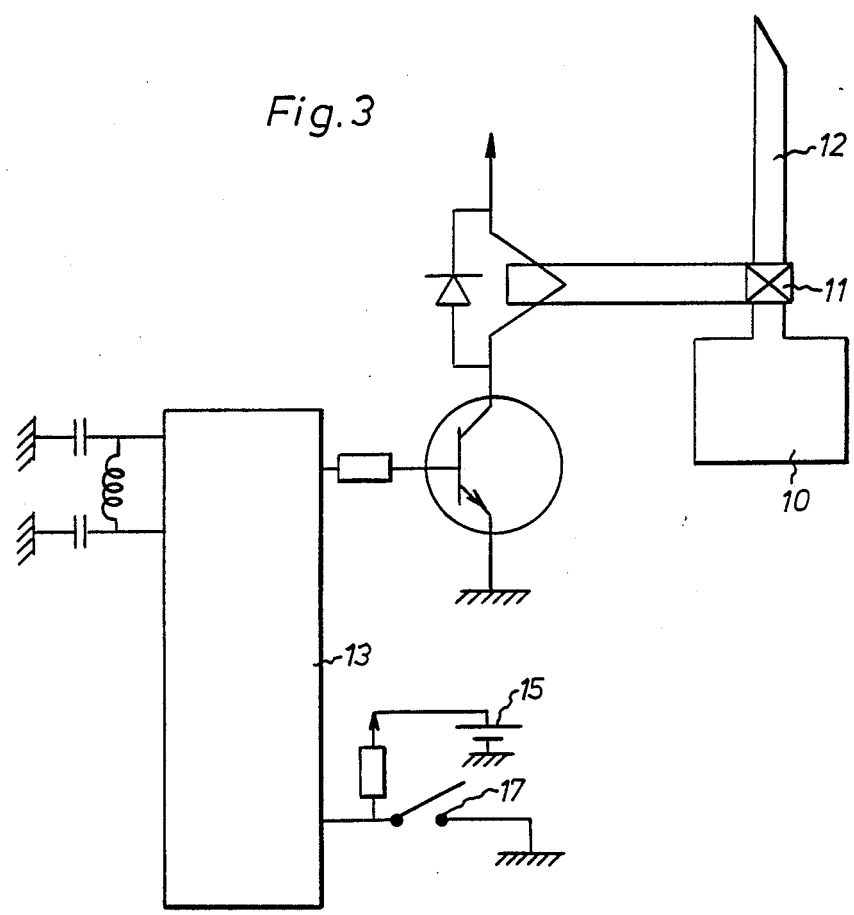
FIG. 3 illustrates the design of the container timing circuit.

The above described embodiment is the simplest one, and slightly more sophisticated embodiments of the invention are described below, reference being had to FIGS. 2 and 3.

An aerosol device according to the invention may comprise one or more gas containers 10 containing different substances, which means that also combinations of different substances can be administered. FIG. 2 shows the design of a generic system of gas containers 10, 10', 10" containing different chemical substances. A common nozzle-forming outlet pipe 12 is supplied with the different substances from the different gas containers 10, 10', 10" via an opening valve 11, 11' and 11", respectively, on each container. An electronic control member which can be activated by means of a switch 17 and is in the form of a control chip 13, controls all activities. Connected to the control chip 13 is, in advanced applications, a display window 14, for example of the LCD type, which supplies information about the number of doses given, if the aerosol can is locked because the maximum dose has been reached and different status conditions, such as low battery voltage 15, prevail. The simpler embodiment according to FIG. 1 may also have such a window 14. The aerosol can may be formed with an input control panel 16 used to control parameters such as dose frequency per unit of time, valve opening time, i.e. dose, so that for example different patients obtain different dose prescriptions with the same aerosol can construction. The supply panel 16 can be designed such that only one programming can be effected, thereby to prevent that the user himself can change the setting. The control chip 13 may be a microcomputer chip or a custom-designed construction. The valve 11, 11', 11'' may be a solenoid type valve with low current consumption, or a silicon-mechanical valve. The valve may also have a small electric motor which constitutes the movable part of a mechanical structure. FIG. 3 illustrates how an aerosol can according . to the invention may be provided with a gas container 10. This embodiment utilises a microcomputer chip 13 which is programmed for this particular use. To give the aerosol can an attractive design, the chip 13 and the valve 11 are formed as a unit, and the battery 15 and the information system 14 are mounted on the outer can periphery for easy access.

EXAMPLE OF APPLICATION

As has been mentioned before, nicotine is one example of a pharmacalogically active substance to which the present invention is applicable. Nicotine is capable of giving unpleasant secondary effects, such as dizziness and feelings of sickness, in subtoxic doses. A nose spray containing nicotine according to the present invention would, as has been mentioned before, be advantageous in that it is more readily applicable and also makes the nicotine take effect more quickly. Overdosing is prevented by correct programming according to the invention. An aerosol pack for a nicotine solution is designed with an extended nozzle or pipe, such that the contents can be supplied in the form of minute droplets or particles of a size such that they are essentially retained in the nose. The timing schedule may be designed such that each depression of the valve will give a dose of 2 mg nicotine. The maximum dose per 30 minutes is set to, for example, 2 or 4 mg. In the first case, a new dose is supplied only after 30 minutes. In the second case, the timing schedule is completed such that, if 30 minutes have not passed between two doses, a new dose is obtained only after another 30 minutes. These timing parameters preferably are fixedly set in a microcomputer or custom-designed chip.

However, the present invention is not restricted to the use of nicotine, but may be applied to a variety of physiologically active substances. For example, insulin, antiallergical drugs, hormones and certain vaccines may be applied by means of a nose spray. A lung spray may be used for the administration of antiasthmatic drugs.

It is even possible to apply the present invention to oral administration of orally administered drugs unsuitable for self-administration. In this instance, the drug is not supplied in the form of an aerosol, but in liquid form, for example a solution, suspension or emulsion, and the opening valve is designed for this purpose.

To the user, the invention is advantageous in that it is readily applicable and provides for rapid absorption of the physiologically active substance. The risk of overdosing can be practically eliminated, and potent drugs can be self-administered.

It will be obvious to the expert that numerous modifications are possible within the scope of the invention as defined by this description and the appended claims.

We claim:

1. A device for self-administration of physiologically active substances without the occurrence of overdosing, comprising:
   a container accommodating at least one substance and propellant means for propelling the substance out of the container;
   nozzle means connected to said container for discharging a substance;
   a valve connected between the nozzle and the container such that a predetermined amount of said substances is propelled from said container each time said valve has been opened; and
   manually activated electronic control means for opening said valve in response to manual activation of said electronic control means and for preventing opening of said valve greater than a predetermined number of times within a predetermined time period.

2. A device for self-administration of physiologically active substances without the occurrence of overdosing, comprising:
   a container accommodating at least one substance and propellant means for propelling the substance out of an outlet of the container;
   a nozzle means connected to said container for discharging a substance;
   a valve connected between the nozzle and the container such that a predetermined amount of said substance is propelled from said outlet of said container each time said valve has been opened, said valve including operating member means relatively manually displaceable with respect to said container for activating said valve upon each displacement thereof;
   mechanical lock means for movement into and out of locking engagement with said operating means or container to prevent relative movement of said operating member means relative to said container; and
   electronic control means for activating said mechanical lock means after a predetermined number of displacements of said operating member and a corresponding number of doses so as to prevent relative movement between said operating member means and said container curing a predetermined time period.

3. A device according to claim 2, wherein said container has a recess and said mechanical lock means is magnetically displaceable between a retracted position and a position in engagement with said recess.

4. A device according to claim 2, further including casing means for displaceably mounting said container therein.

* * * * *